US008859570B2

(12) United States Patent
McCabe

(10) Patent No.: US 8,859,570 B2
(45) Date of Patent: Oct. 14, 2014

(54) MALEATE SALTS OF A QUINAZOLINE DERIVATIVE USEFUL AS AN ANTIANGIOGENIC AGENT

(75) Inventor: James McCabe, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 981 days.

(21) Appl. No.: 12/646,153

(22) Filed: Dec. 23, 2009

(65) Prior Publication Data

US 2010/0298357 A1    Nov. 25, 2010

Related U.S. Application Data

(63) Continuation of application No. 10/581,279, filed as application No. PCT/GB2004/005359 on Dec. 18, 2004, now abandoned.

(30) Foreign Application Priority Data

Dec. 24, 2003 (GB) .................................. 0330002.7

(51) Int. Cl.
*A01N 43/54* (2006.01)
*A61K 31/517* (2006.01)
*C07D 239/72* (2006.01)
*C07D 401/00* (2006.01)

(52) U.S. Cl.
USPC ........................ 514/266.2; 544/283; 544/284

(58) Field of Classification Search
USPC ................................ 514/266.2; 544/283, 284
See application file for complete search history.

(56) References Cited

U.S. PATENT DOCUMENTS

| 5,409,930 | A | 4/1995 | Spada et al. |
| 5,411,963 | A | 5/1995 | Dreilcorn et al. |
| 5,480,883 | A | 1/1996 | Spada et al. |
| 5,646,153 | A | 7/1997 | Spada et al. |
| 5,710,158 | A | 1/1998 | Myers et al. |
| 5,714,493 | A | 2/1998 | Myers et al. |
| 5,721,237 | A | 2/1998 | Myers et al. |
| 5,736,534 | A | 4/1998 | Arnold et al. |
| 5,859,009 | A | 1/1999 | Schaper et al. |
| RE36,256 | E | 7/1999 | Spada et al. |
| 6,046,206 | A | 4/2000 | Pamukcu et al. |
| 6,057,320 | A | 5/2000 | Spada et al. |
| 6,153,617 | A | 11/2000 | Bridges |
| 6,162,804 | A | 12/2000 | Bilodeau et al. |
| 6,225,318 | B1 | 5/2001 | Sobolov-Jaynes et al. |
| 6,531,491 | B1 | 3/2003 | Kania et al. |
| 6,645,969 | B1 | 11/2003 | Myers et al. |
| 7,074,800 | B1 | 7/2006 | Stokes et al. |
| 2002/0177601 | A1 | 11/2002 | Himmelsbach et al. |
| 2008/0125447 | A1 | 5/2008 | Wedge |
| 2009/0028943 | A1 | 1/2009 | Cahill et al. |

FOREIGN PATENT DOCUMENTS

| DE | 19614718 | 10/1997 |
| EP | 0326330 | 8/1989 |
| EP | 0602851 | 6/1994 |
| EP | 0837063 | 4/1998 |
| EP | 1029853 | 8/2000 |
| GB | 2345486 | 7/2000 |
| JP | 2002536414 | 10/2002 |
| JP | 2003528917 A1 | 9/2003 |
| WO | WO 87/04321 | 7/1987 |
| WO | WO 92/20642 | 11/1992 |
| WO | WO 95/15758 | 6/1995 |
| WO | WO 95/19169 | 7/1995 |
| WO | WO 95/23141 | 8/1995 |
| WO | WO 95/24190 | 9/1995 |
| WO | WO 96/29301 | 9/1996 |
| WO | WO 96/39145 | 12/1996 |
| WO | WO 97/03069 | 1/1997 |
| WO | WO 97/17329 | 5/1997 |
| WO | WO 97/22596 | 6/1997 |
| WO | WO 97/30034 | 8/1997 |
| WO | WO 97/42187 | 11/1997 |
| WO | WO 98/02434 | 1/1998 |
| WO | WO 98/54093 | 12/1998 |
| WO | WO 99/06396 | 2/1999 |
| WO | WO 99/10349 | 3/1999 |
| WO | WO 99/21859 | 5/1999 |
| WO | WO 99/35132 | 7/1999 |
| WO | WO 99/35146 | 7/1999 |
| WO | WO 00/06554 | 2/2000 |
| WO | WO 00/12497 | 3/2000 |
| WO | WO 00/44728 | 8/2000 |
| WO | WO 00/47212 | 8/2000 |
| WO | WO 00/55141 | 9/2000 |
| WO | WO 01/02369 | 1/2001 |
| WO | WO 01/29025 | 4/2001 |
| WO | 03014732 A1 | 2/2003 |
| WO | 03064413 A1 | 8/2003 |

OTHER PUBLICATIONS

Bridges et al. "Enantioselective Inhibition of the Epidermal Growth Factor Receptor Tyrosine Kinase by a 4-(a-Phenethylamino)quinazolines" Bioorganic & Medicinal Chemistry 3(12):1651-1656 (1995).

(Continued)

*Primary Examiner* — Paul V. Ward

(74) *Attorney, Agent, or Firm* — Morgan, Lewis & Bockius LLP

(57) ABSTRACT

The present invention relates to AZD2171 maleate salt, to particular crystalline forms of AZD2171 maleate salt, to processes for their preparation, to pharmaceutical compositions containing them as active ingredient, to their use in the manufacture of medicaments for use in the production of antiangiogenic and/or vascular permeability reducing effects in warm-blooded animals such as humans, and to their use in methods for the treatment of disease states associated with angiogenesis and/or increased vascular permeability.

11 Claims, 10 Drawing Sheets

(56) References Cited

OTHER PUBLICATIONS

Gazit et al. "Tyrophostins IV-Highly Potent Inhibitors of EGF Receptor Kinase. Structure-Activity Relationship Study of 4-Anilidoquinazolines" Bioorganic & Medicinal Chemistry 4(8): 1203-1207 (1996).

Gibson et al., "Epidermal growth factor receptor tyrosine kinase: structure-activity relationships and antitumour activity of novel quinazolines" Bioorganic & Medicinal Chemistry 7(21):2723-2728 (1997).

Hara et al., "On the Amination of Azaheterocycles. A New Procedure for the Introduction of an Amino Group (1)" J. Heterocyclic Chem. 19:1285-1287 (1982).

Hennequin et al., "Design and Structure Activity Relationship of a New Class of Potent VEGF Receptor Tyrosine Kinase Inhibitors" Journal of Medicinal Chemistry, American Chemical Society 42: 5369-5389 (1999).

Karminski et al., Chemical Abstracts, vol. 100: 34492 (1984).

Karminski et al. "The Synthesis of Some Quinazoline Derivatives and Their Biological Properties" J. Environ. Sci. Health B18: 599-610 (1983).

Sinyak et al., Chemical Abstracts, vol. 140: 199594 (1986).

Sinyak et al. "Synthesis and Biological Properties of Derivatives of 4-Heterylmercaptoquinazoline" Zaporozh'e Medical Institute pp. 103-106, translated from Khimiko-farmatsevticheskii Zhurnal, vol. 20, No. 2, Feb. 1986, 168-171.

Zwick et al. "Receptor tyrosine kinase signalling as a target for cancer intervention strategies" Endocrine-Related Cancer 8(3):161-173 (2001).

"Guidelines for Residual Solvents in Drug Products," Ministerial Notification No. 307 by Director, Evaluation and Licensing Division; Pharmaceutical and Medical Safety Bureau; MLHW (1998) (English language abstract only).

"Guidelines for Specifications and Testing Methods of New Drug Products," Ministerial Notification No. 568 by Director, Evaluation and Licensing Division; Pharmaceutical and Medical Safety Bureau; MLHW (2001) (English language abstract only).

Matsuoka, Masakuni, Advanced Crystallization Technology of Organic Materials—Control of Size, Morphology, Polymorph and Purity—, Pharm. Tech. Japan; (May 1, 2003); vol. 19; No. 6, p. 91 (955) to 101 (965) (English language abstract only).

Yamamoto, Eiji, et al., Crystal Polymorphism and Separation Operation, Bunri Gijutsu (Separation Process Engineering) (1995); vol. 25; No. 5 (No. 127); p. 9 (381) to 38 (410) (English language abstract only).

Bastin et al., "Salt Selection and Optimisation Procedures for Pharmaceutical New Chemical Entities," Organic Process Research & Development, 4: 427-435 (2000).

Brittain, H.G., "Polymorphism in Pharmaceutical Solids," Theory and Origin of Polymorphism (1998-1999), (see abstract).

Written Opinion and International Preliminary Report on Patentability issued in related International Patent Application No. PCT/GB2004/005359 dated Jul. 6, 2006.

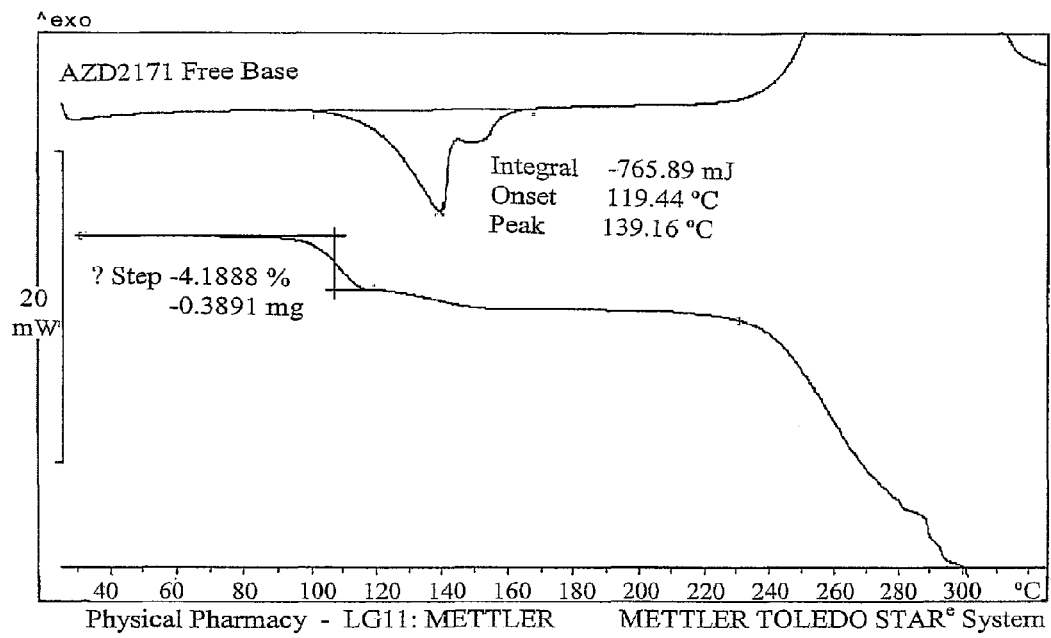
Figure 1: DSC and TGA Thermograms AZD2171 Free base Monohydrate

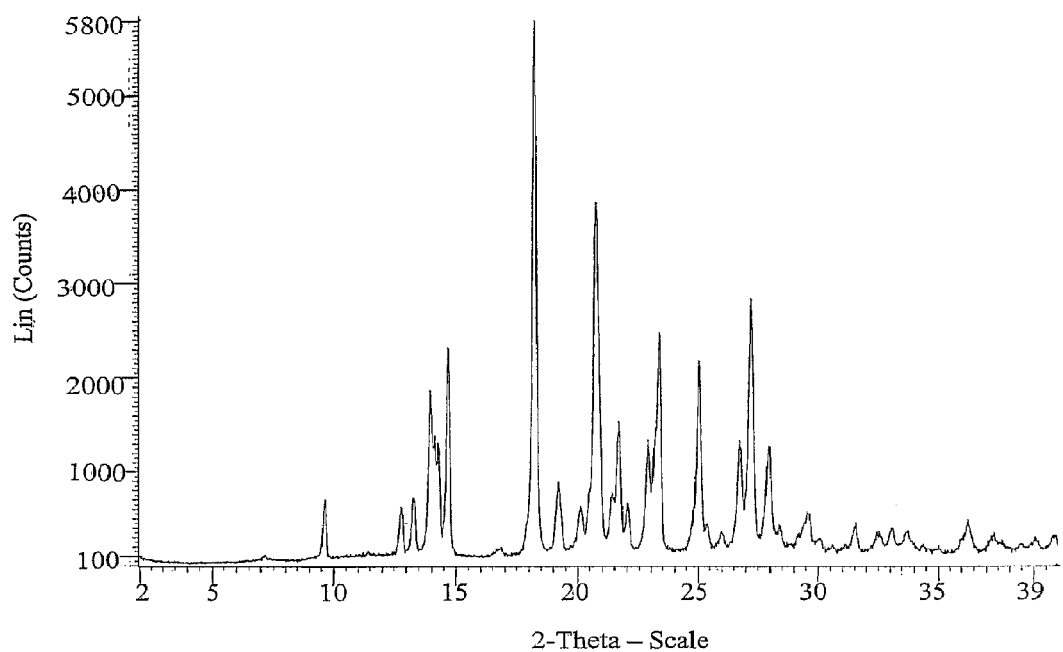
Figure 2: X-Ray Powder Diffraction Pattern AZD2171 free base

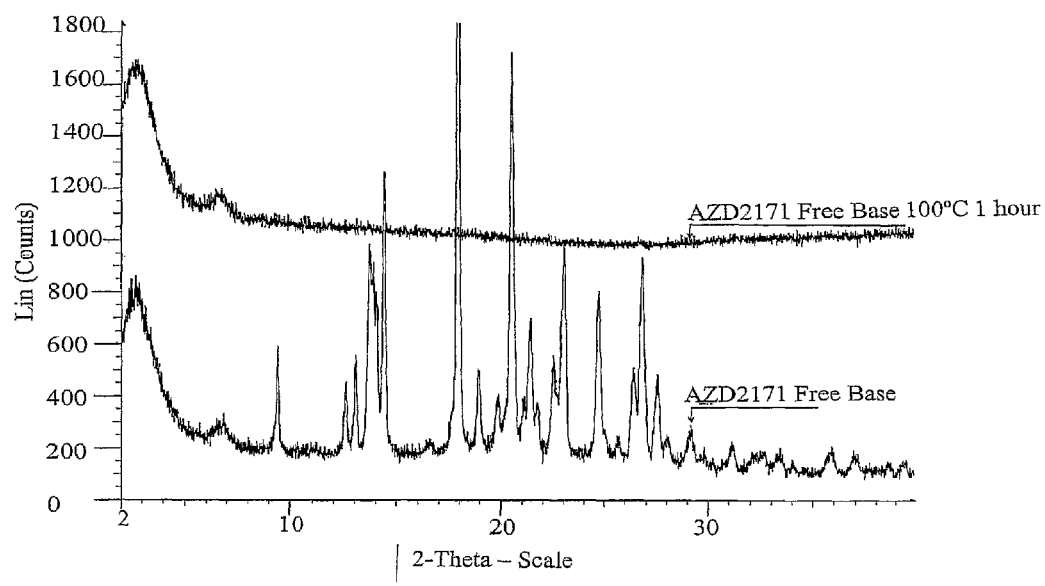
Figure 3: X-Ray Powder Diffraction Pattern AZD2171 Free base Monohydrate Heated to 100° C

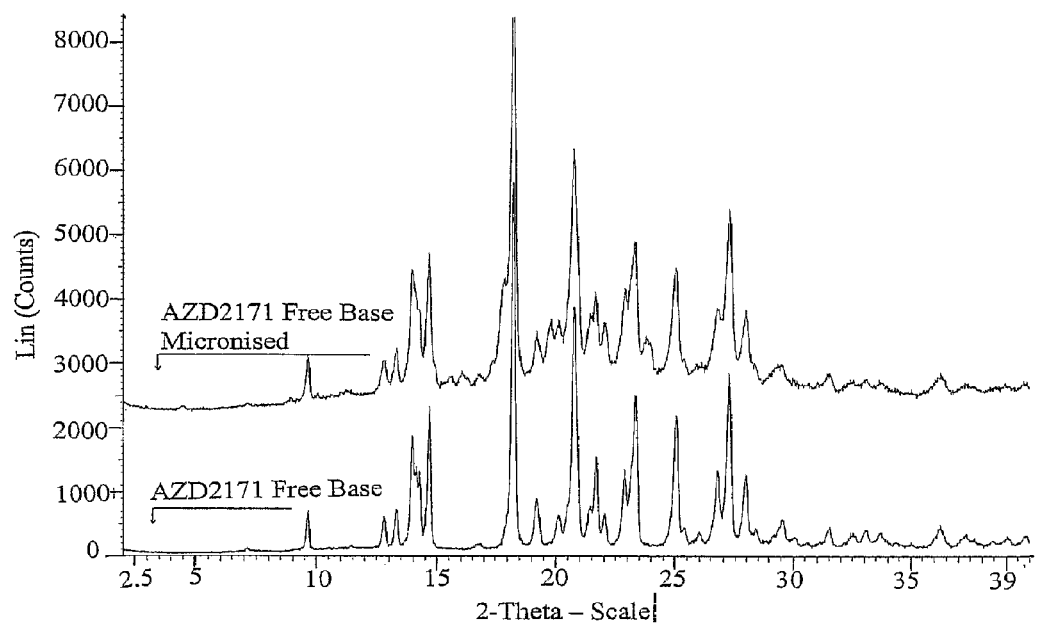
Figure 4: X-Ray Powder Diffraction Pattern AZD2171 Free base Micronised

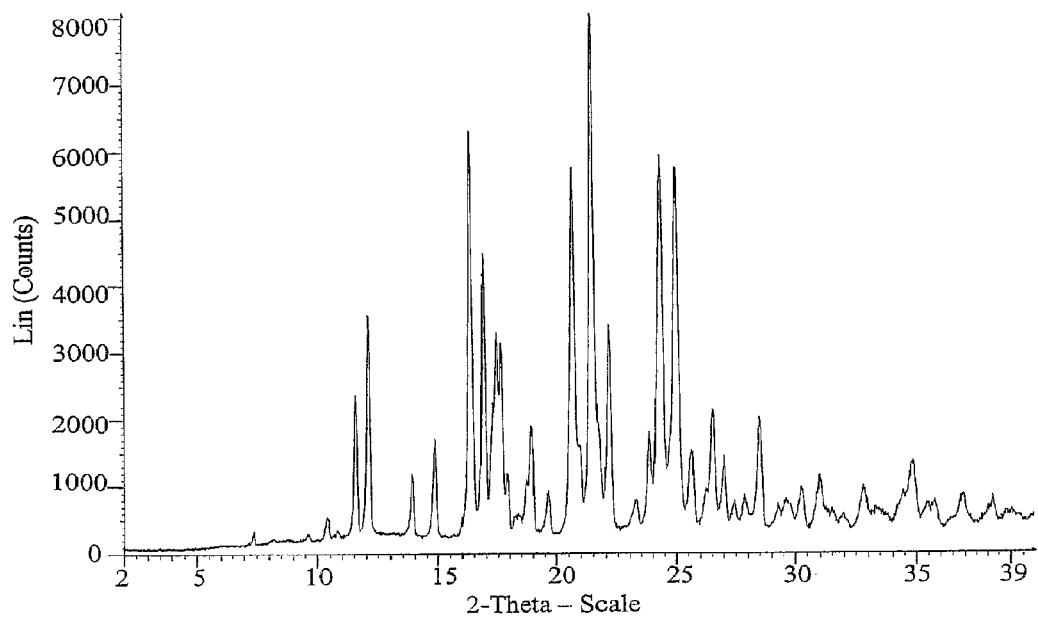
Figure 5: X-Ray Powder Diffraction Pattern AZD2171 Maleate Salt Form A

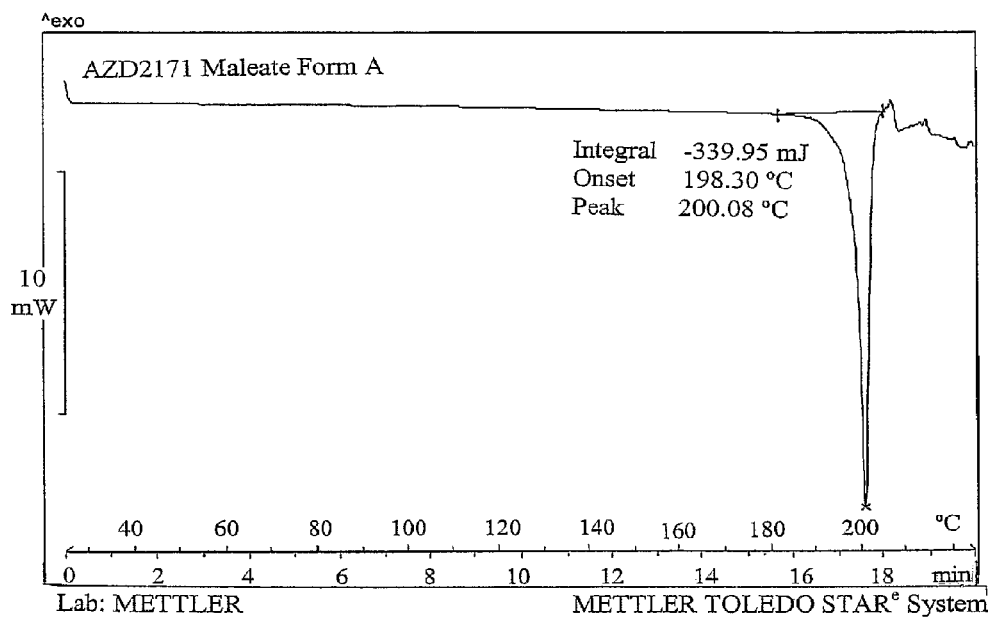
Figure 6: DSC Thermogram AZD2171 Maleate Form A

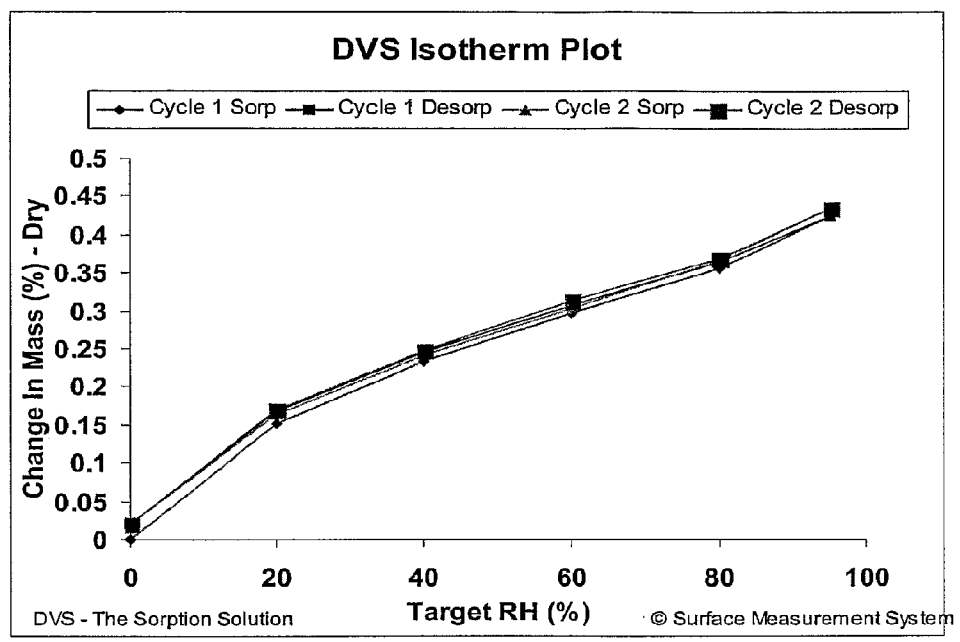
Figure 7: AZD2171 Maleate Form A Vapour Sorption Isotherm at 25° C

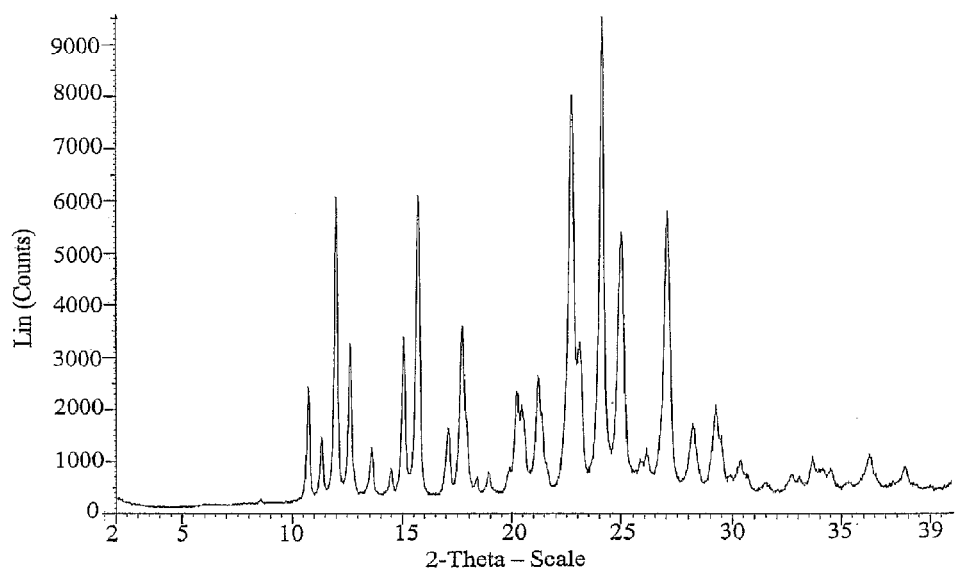
Figure 8: X-Ray Powder Diffraction Pattern AZD2171 Maleate Salt Form B

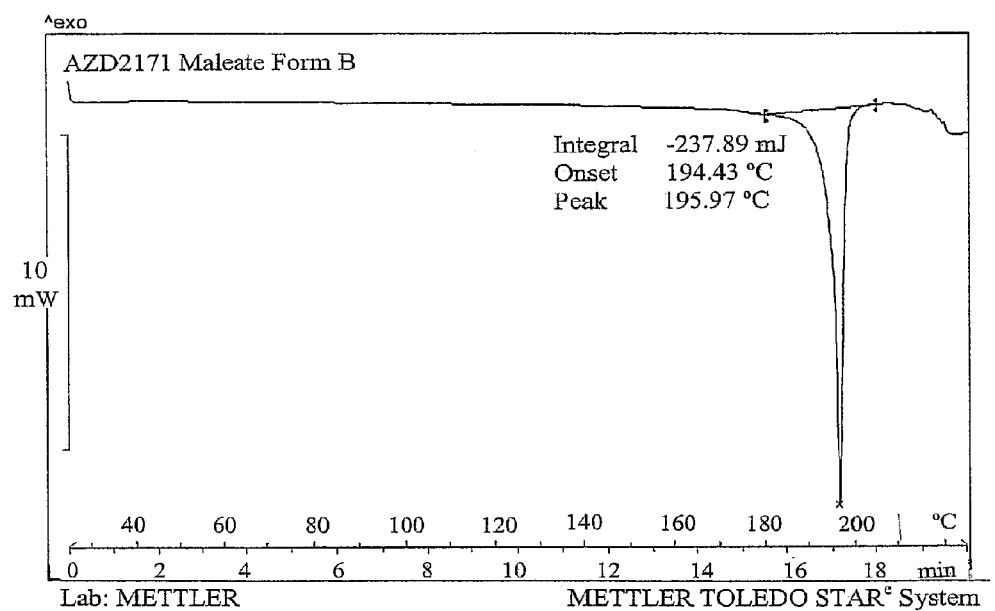
Figure 9: DSC Thermogram AZD2171 Maleate Form B

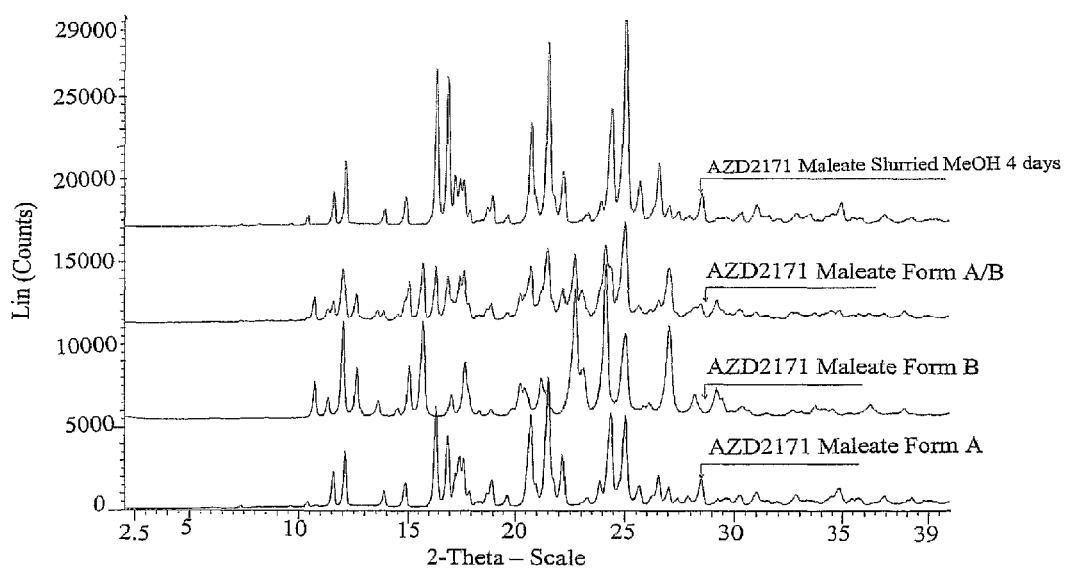
Figure 10: X-Ray Powder Diffraction Patterns AZD2171 Maleate Slurry Experiment

MALEATE SALTS OF A QUINAZOLINE DERIVATIVE USEFUL AS AN ANTIANGIOGENIC AGENT

The present invention relates to AZD2171 maleate salt, to particular crystalline forms of AZD2171 maleate salt, to processes for their preparation, to pharmaceutical compositions containing them as active ingredient, to their use in the manufacture of medicaments for use in the production of antiangiogenic and/or vascular permeability reducing effects in warm-blooded animals such as humans, and to their use in methods for the treatment of disease states associated with angiogenesis and/or increased vascular permeability.

Normal angiogenesis plays an important role in a variety of processes including embryonic development, wound healing and several components of female reproductive function. Undesirable or pathological angiogenesis has been associated with disease states including diabetic retinopathy, psoriasis, cancer, rheumatoid arthritis, atheroma, Kaposi's sarcoma and haemangioma (Fan et al, 1995, Trends Pharmacol. Sci. 16: 57-66; Folkman, 1995, Nature Medicine 1: 27-31). Alteration of vascular permeability is thought to play a role in both normal and pathological physiological processes (Cullinan-Bove et al, 1993, Endocrinology 133: 829-837; Senger et al, 1993, Cancer and Metastasis Reviews, 12: 303-324). Several polypeptides with in vitro endothelial cell growth promoting activity have been identified including, acidic and basic fibroblast growth factors (aFGF & bFGF) and vascular endothelial growth factor (VEGF). By virtue of the restricted expression of its receptors, the growth factor activity of VEGF, in contrast to that of the FGFs, is relatively specific towards endothelial cells. Recent evidence indicates that VEGF is an important stimulator of both normal and pathological angiogenesis (Jakeman et al, 1993, Endocrinology, 133: 848-859; Kolch et al, 1995, Breast Cancer Research and Treatment, 36:139-155) and vascular permeability (Connolly et al, 1989, J. Biol. Chem. 264: 20017-20024). Antagonism of VEGF action by sequestration of VEGF with antibody can result in inhibition of tumour growth (Kim et al, 1993, Nature 362: 841-844).

Receptor tyrosine kinases (RTKs) are important in the transmission of biochemical signals across the plasma membrane of cells. These transmembrane molecules characteristically consist of an extracellular ligand-binding domain connected through a segment in the plasma membrane to an intracellular tyrosine kinase domain. Binding of ligand to the receptor results in stimulation of the receptor-associated tyrosine kinase activity which leads to phosphorylation of tyrosine residues on both the receptor and other intracellular molecules. These changes in tyrosine phosphorylation initiate a signalling cascade leading to a variety of cellular responses. To date, at least nineteen distinct RTK subfamilies, defined by amino acid sequence homology, have been identified. One of these subfamilies is presently comprised by the fms-like tyrosine kinase receptor, Flt-1, the kinase insert domain-containing receptor, KDR (also referred to as Flk-1), and another fms-like tyrosine kinase receptor, Flt-4. Two of these related RTKs, Flt-1 and KDR, have been shown to bind VEGF with high affinity (De Vries et al, 1992, Science 255: 989-991; Terman et al, 1992, Biochem. Biophys. Res. Comm. 1992, 187: 1579-1586). Binding of VEGF to these receptors expressed in heterologous cells has been associated with changes in the tyrosine phosphorylation status of cellular proteins and calcium fluxes.

VEGF is a key stimulus for vasculogenesis and angiogenesis. This cytokine induces a vascular sprouting phenotype by inducing endothelial cell proliferation, protease expression and migration, and subsequent organisation of cells to form a capillary tube (Keck, P. J., Hauser, S. D., Krivi, G., Sanzo, K., Warren, T., Feder, J., and Connolly, D. T., Science (Washington D.C.), 246: 1309-1312, 1989; Lamoreaux, W. J., Fitzgerald, M. E., Reiner, A., Hasty, K. A., and Charles, S. T., Microvasc. Res., 55: 29-42, 1998; Pepper, M. S., Montesano, R., Mandroita, S. J., Orci, L. and Vassalli, J. D., Enzyme Protein, 49: 138-162, 1996.). In addition, VEGF induces significant vascular permeability (Dvorak, H. F., Detmar, M., Claffey, K. P., Nagy, J. A., van de Water, L., and Senger, D. R., (Int. Arch. Allergy Immunol., 107: 233-235, 1995; Bates, D. O., Heald, R. I., Curry, F. E. and Williams, B. J. Physiol. (Lond.), 533: 263-272, 2001), promoting formation of a hyper-permeable, immature vascular network which is characteristic of pathological angiogenesis.

It has been shown that activation of KDR alone is sufficient to promote all of the major phenotypic responses to VEGF, including endothelial cell proliferation, migration, and survival, and the induction of vascular permeability (Meyer, M., Clauss, M., Lepple-Wienhues, A., Waltenberger, J., Augustin, H. G., Ziche, M., Lanz, C., Büttner, M., Rziha, H-J., and Dehio, C., EMBO J., 18: 363-374, 1999; Zeng, H., Sanyal, S, and Mukhopadhyay, D., J. Biol. Chem., 276: 32714-32719, 2001; Gille, H., Kowalski, J., Li, B., LeCouter, J., Moffat, B, Zioncheck, T. F., Pelletier, N. and Ferrara, N., J. Biol. Chem., 276: 3222-3230, 2001).

Compounds which inhibit the effects of VEGF are of value in the treatment of disease states associated with angiogenesis and/or increased vascular permeability such as cancer (including leukaemia, multiple myeloma and lymphoma), diabetes, psoriasis, rheumatoid arthritis, Kaposi's sarcoma, haemangioma, acute and chronic nephropathies, atheroma, arterial restenosis, autoimmune diseases, acute inflammation, excessive scar formation and adhesions, endometriosis, lymphoedema, dysfunctional uterine bleeding and ocular diseases with retinal vessel proliferation including macular degeneration.

Quinazoline derivatives which are inhibitors of VEGF receptor tyrosine kinase are described in WO 00/47212. The compound AZD2171 is exemplified in WO 00/47212, (see Example 240), and is 4-((4-fluoro-2-methyl-1H-indol-5-yl)oxy)-6-methoxy-7-(3-(pyrrolidin-1-yl)propoxy)quinazoline of the formula I:

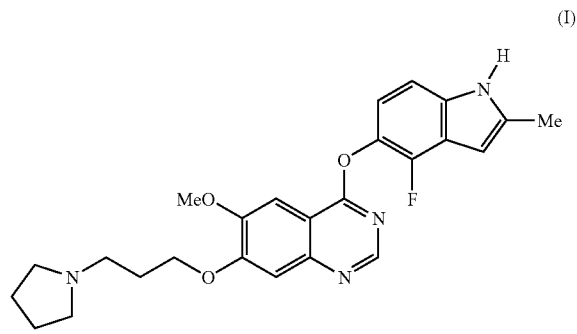 [SMILES: COc1cc2c(Oc3ccc4[nH]c(C)cc4c3F)ncnc2cc1OCCCN1CCCC1]

(I)

AZD2171 shows excellent activity in the in vitro (a) enzyme and (b) HUVEC assays that are described in WO 00/47212 and hereinafter. The AZD2171 $IC_{50}$ values for inhibition of isolated KDR (VEGFR-2) and Flt-1 (VEGFR-1) tyrosine kinase activities in the enzyme assay were <2 nM and 5±2 nM respectively. AZD2171 inhibits VEGF-stimulated endothelial cell proliferation potently ($IC_{50}$ value of 0.4±0.2 nM in the HUVEC assay), but does not inhibit basal endothelial cell proliferation appreciably at a >1250 fold greater concentration (IC$_{50}$ value is >500 nM). The growth of a Calu-6 tumour xenograft in the in vivo (c) solid tumour model described hereinafter was inhibited by 49%, 69%* and 91%* following 28 days of once-daily oral treatment with 1.5, 3 and 6 mg/kg/day AZD2171 respectively (P<0.01, P***<0.0001; one-tailed t test).

More stable forms of a pharmaceutically active compound, for example more stable crystalline forms, are preferred for formulation and processing on a commercial scale. This is because the greater the stability of the form used, the lower the risk of it converting to another form during formulation procedures such as compression. This in turn provides greater predictability of the properties of the final formulation, such as dissolution rate of tablets, bioavailability of active ingredient. Using a more stable form of an active ingredient allows greater control over the physical properties of the formulation.

AZD2171 free base (4-((4-fluoro-2-methyl-1H-indol-5-yl)oxy)-6-methoxy-7-(3-(pyrrolidin-1-yl)propoxy)quinazoline) is a crystalline monohydrate under ambient conditions. Differential Scanning calorimetry (DSC) analysis was carried out according to the method described hereinafter and shows a large broad endotherm between 95° and 170° C. due to loss of water and melting (FIG. 1). Thermogravimetric (TGA) analysis (details given hereinafter) shows a weight loss of 4.02% between 80° C. and 115° C. (FIG. 1). Karl Fischer water analysis (details given hereinafter) yields a figure of 3.9% suggesting that all the weight loss is due to water loss.

It will be understood that the onset/peak temperature values of the DSC may vary slightly from one machine to another or from one sample to another, and so the values quoted are not to be construed as absolute.

AZD2171 free base is characterised in providing at least one of the following 2θ values measured using CuKa radiation: 18.3 and 20.8. AZD2171 free base is characterised in providing an X-ray powder diffraction pattern, as in FIG. 2. The ten most prominent peaks are shown in Table 1.

TABLE 1

Ten most Prominent X-Ray Powder Diffraction peaks for AZD2171 free base

| Angle 2-Theta (2θ) | Intensity Count | Relative Intensity |
|---|---|---|
| 18.287 | 100 | vs |
| 20.807 | 66.7 | vs |
| 27.277 | 48.9 | vs |
| 23.370 | 42.8 | vs |
| 14.684 | 39.8 | vs |
| 25.070 | 37.6 | vs |
| 13.966 | 32.2 | vs |
| 21.711 | 26.6 | vs |
| 22.898 | 23.1 | vs |
| 26.790 | 22.9 | vs | vs = very strong

It has been found that when a sample of AZD2171 free base is dehydrated, for example on heating to 100° C., the sample becomes amorphous (FIG. 3) and does not then rehydrate but stays amorphous thereafter. This could be problematic if AZD2171 free base were to be formulated as a pharmaceutical composition because AZD2171 free base could dehydrate during certain processes e.g. particle size reduction (such as milling), drying of bulk drug, formulating, manufacturing. In order to formulate AZD2171 free base as a pharmaceutical composition it would be necessary to reduce the particle size at some point, and this would carry a risk of dehydration and therefore the risk of the formation of amorphous material. This was investigated by subjecting a sample of AZD2171 free base monohydrate to particle size reduction by micronisation and then analysing it to look for amorphous material. FIG. 4 shows that amorphous material does indeed form during particle size reduction of AZD2171 free base. This is shown by a broadening of the peaks and formation of an amorphous 'hump'—see FIG. 4. An amorphous or semi-amorphous form of AZD2171 free base could give rise to manufacturing problems and non-reproducible bioavailability.

The identification of alternative forms of AZD2171, forms that are different from the free base and that have improved solid state properties, is the subject of the present invention.

An example of a different form is a salt of AZD2171. In WO 00/47212 it says that pharmaceutically acceptable salts of the compounds of the invention therein may include acid addition salts of the compounds of the invention which are sufficiently basic to form such salts. Such acid addition salts are said to include salts with inorganic or organic acids affording pharmaceutically acceptable anions such as with hydrogen halides especially hydrochloric or hydrobromic acid or with sulphuric or phosphoric acid, or with trifluoroacetic, citric or maleic acid. In addition WO 00/47212 goes on to say that where the compounds of the invention therein are sufficiently acidic, pharmaceutically acceptable salts may be formed with an inorganic or organic base which affords a pharmaceutically acceptable cation. Such salts with inorganic or organic bases are said to include an alkali metal salt, such as a sodium or potassium salt, an alkaline earth metal salt such as a calcium or magnesium salt, an ammonium salt or for example a salt with methylamine, dimethylamine, trimethylamine, piperidine, morpholine or tris-(2-hydroxyethyl) amine.

Preferred salts in WO 00/47212 are hydrochlorides and hydrobromides, especially hydrochlorides.

Nowhere in WO 00/47212 does it state that a particular salt of a particular compound therein will possess surprisingly beneficial properties.

Unexpectedly and surprisingly we have now found that the maleate salt of AZD2171 is an advantageously stable form of AZD2171 with improved solid state properties over the free base and over other salts that have been tested.

AZD2171 maleate is readily crystallised, is highly crystalline, non-hygroscopic and has a reproducible stoichiometric ratio of drug to counter-ion of 1:1.

Thus AZD2171 maleate is readily crystallised, is highly crystalline, non-hygroscopic and has a reproducible stoichiometric ratio of drug to counter-ion of about 1:1.

Several salts of AZD2171 were prepared and seven were found to be crystalline: malonate, succinate, fumarate, maleate, tartarate, adipate and malate. The solid state properties of these 7 salts were tested and the results are shown in Table 2:

TABLE 2

Properties of AZD2171 Salts

| Salt | Crystalline (Yes/No) | Drug:Counterion Stoichiometry$^a$ | Moisture Content at 80% RH$^b$ | Evidence of Hydrate Formation$^b$ (Yes/No) | No of Polymorphs$^c$ |
|---|---|---|---|---|---|
| Malonate | Yes | — | — | Yes | ≥3 |
| Succinate | Yes | 1:0.63 | 11.4 | No | ≥2 |
| Fumarate | Yes | 1:0.5 | 3.5 | No | ≥3 |
| Maleate | Yes | 1:1 | 0.4 | No | ≥2 |
| Tartarate | Yes | 1:0.75 | 9.3 | No | ≥1 |

TABLE 2-continued

Properties of AZD2171 Salts

| Salt | Crystal-line (Yes/No) | Drug:Coun-terion Stoichio-metry[a] | Moisture Content at 80% RH[b] | Evidence of Hydrate Formation[b] (Yes/No) | No of Poly-morphs[c] |
|---|---|---|---|---|---|
| Adipate | Yes | 1:0.75 | — | No | ≥3 |
| Malate | Yes | — | 7.7 | Yes | — |

[a]Drug:counterion stoichiometry from ¹H NMR Spectrum data
[b]Moisture content at 80% relative humidity (RH). Evidence of hydration from Vapour Sorption studies (observed hysteresis and absorption of water) or Thermogravimetric Analysis (TGA)
[c]Evidence for polymorphism from Differential Scanning Calorimetry (DSC) thermograms
The term 'non-hygroscopic' means absorbing <1% moisture at 80% RH.

The AZD2171 maleate salt was surprisingly better than the others because of the 7 salts that it was possible to crystallise, it was found to be the only non-hygroscopic salt, to be highly crystalline and to have a reproducible stoichiometric ratio of drug to counter-ion of 1:1.

Thus AZD2171 maleate was found to be the only non-hygroscopic salt, to be highly crystalline and to have a reproducible stoichiometric ratio of drug to counter-ion of about 1:1.

AZD2171 maleate salt is substantially free of amorphous material and can be expected to be easier to formulate than AZD2171 free base and to provide more reproducible dosing results. By "substantially free of amorphous material" is meant that the amount of amorphous material is less than 10%, preferably less than 5%, more preferably less than 2%.

AZD2171 maleate salt is non-hygroscopic which should prevent or reduce any problems associated with weight changes of the active ingredient during procedures such as micronisation.

According to the present invention there is provided a maleate salt of AZD2171.

AZD2171 maleate has two crystalline forms A and B.

According to the present invention there is provided a maleate salt of AZD2171 in a first crystalline form, Form A.

AZD2171 Maleate Form A is characterised in providing at least one of the following 2θ values measured using CuKa radiation: 21.5 and 16.4. AZD2171 Maleate Form A is characterised in providing an X-ray powder diffraction pattern, substantially as shown in FIG. 5. The ten most prominent peaks are shown in Table 3:

TABLE 3

Ten most Prominent X-Ray Powder Diffraction peaks for AZD2171 Maleate Form A

| Angle 2-Theta (2θ) | Intensity Count | Relative Intensity |
|---|---|---|
| 21.522 | 100 | vs |
| 16.366 | 78.3 | vs |
| 24.381 | 73.7 | vs |
| 20.721 | 71.7 | vs |
| 25.025 | 71.5 | vs |
| 16.921 | 55.5 | vs |
| 12.085 | 44.1 | vs |
| 22.177 | 42.2 | vs |
| 17.444 | 40.7 | vs |
| 17.627 | 39.1 | vs | vs = very strong

According to the present invention there is provided a maleate salt of AZD2171 in a first crystalline form, Form A, wherein said salt has an X-ray powder diffraction pattern with at least one specific peak at about 2-theta=21.5°.

According to the present invention there is provided a maleate salt of AZD2171 in a first crystalline form, Form A, wherein said salt has an X-ray powder diffraction pattern with at least one specific peak at about 2-theta=16.4°.

According to the present invention there is provided a maleate salt of AZD2171 in a first crystalline form, Form A, wherein said salt has an X-ray powder diffraction pattern with at least two specific peaks at about 2-theta=21.5° and 16.4°.

According to the present invention there is provided a maleate salt of AZD2171 in a first crystalline form, Form A, wherein said salt has an X-ray powder diffraction pattern with specific peaks at about 2-theta=21.5, 16.4, 24.4, 20.7, 25.0, 16.9, 12.1, 22.2, 17.4 and 17.6°.

According to the present invention there is provided a maleate salt of AZD2171 in a first crystalline form, Form A, wherein said salt has an X-ray powder diffraction pattern substantially the same as the X-ray powder diffraction pattern shown in FIG. 5.

According to the present invention there is provided a maleate salt of AZD2171 in a first crystalline form, Form A, wherein said salt has an X-ray powder diffraction pattern with at least one specific peak at 2-theta=21.5° plus or minus 0.5° 2-theta.

According to the present invention there is provided a maleate salt of AZD2171 in a first crystalline form, Form A, wherein said salt has an X-ray powder diffraction pattern with at least one specific peak at 2-theta=16.4° plus or minus 0.5° 2-theta.

According to the present invention there is provided a maleate salt of AZD2171 in a first crystalline form, Form A, wherein said salt has an X-ray powder diffraction pattern with at least two specific peaks at 2-theta=21.5° and 16.4° wherein said values may be plus or minus 0.5° 2-theta.

According to the present invention there is provided a maleate salt of AZD2171 in a first crystalline form, Form A, wherein said salt has an X-ray powder diffraction pattern with specific peaks at 2-theta=21.5, 16.4, 24.4, 20.7, 25.0, 16.9, 12.1, 22.2, 17.4 and 17.6° wherein said values may be plus or minus 0.5° 2-theta.

According to the present invention there is provided a maleate salt of AZD2171 in a first crystalline form, Form A, wherein said salt has an X-ray powder diffraction pattern with at least one specific peak at 2-theta=21.5°.

According to the present invention there is provided a maleate salt of AZD2171 in a first crystalline form, Form A, wherein said salt has an X-ray powder diffraction pattern with at least one specific peak at 2-theta=16.4°.

According to the present invention there is provided a maleate salt of AZD2171 in a first crystalline form, Form A, wherein said salt has an X-ray powder diffraction pattern with at least two specific peaks at 2-theta=21.5° and 16.4°.

According to the present invention there is provided a maleate salt of AZD2171 in a first crystalline form, Form A, wherein said salt has an X-ray powder diffraction pattern with specific peaks at 2-theta=21.5, 16.4, 24.4, 20.7, 25.0, 16.9, 12.1, 22.2, 17.4 and 17.6°.

According to the present invention there is provided a maleate salt of AZD2171 in a first crystalline form, Form A, wherein said salt has an X-ray powder diffraction pattern as shown in FIG. 5.

DSC analysis shows AZD2171 maleate Form A is a high melting solid with an onset of melting at 198.3° C. and a peak at 200.08° C. (FIG. 6).

Thus DSC analysis shows AZD2171 maleate Form A is a high melting solid with an onset of melting at about 198.3° C. and a peak at about 200.08° C.

According to the present invention there is provided a maleate salt of AZD2171 in a second crystalline form, Form B.

AZD2171 Maleate Form B is characterised in providing at least one of the following 2θ values measured using CuKa radiation: 24.2 and 22.7. AZD2171 Maleate Form B is characterised in providing an X-ray powder diffraction pattern substantially as shown in FIG. 8. The ten most prominent peaks are shown in Table 4:

TABLE 4

Ten most Prominent X-Ray Powder Diffraction peaks for AZD2171 Maleate Form B

| Angle 2-Theta (2θ) | Intensity Count | Relative Intensity |
| --- | --- | --- |
| 24.156 | 100 | vs |
| 22.740 | 84.3 | vs |
| 15.705 | 64.0 | vs |
| 11.995 | 63.7 | vs |
| 27.087 | 60.9 | vs |
| 25.032 | 56.8 | vs |
| 17.724 | 37.7 | vs |
| 15.044 | 35.4 | vs |
| 23.102 | 34.5 | vs |
| 12.625 | 34.2 | vs | vs = very strong

According to the present invention there is provided a maleate salt of AZD2171 in a second crystalline form, Form B, wherein said salt has an X-ray powder diffraction pattern with at least one specific peak at about 2-theta=24.2°.

According to the present invention there is provided a maleate salt of AZD2171 in a second crystalline form, Form B, wherein said salt has an X-ray powder diffraction pattern with at least one specific peak at about 2-theta=22.7°.

According to the present invention there is provided a maleate salt of AZD2171 in a second crystalline form, Form B, wherein said salt has an X-ray powder diffraction pattern with at least two specific peaks at about 2-theta=24.2° and 22.7°.

According to the present invention there is provided a maleate salt of AZD2171 in a second crystalline form, Form B, wherein said salt has an X-ray powder diffraction pattern with specific peaks at about 2-theta=24.2, 22.7, 15.7, 12.0, 27.1, 25.0, 17.7, 15.0, 23.1 and 12.6°.

According to the present invention there is provided a maleate salt of AZD2171 in a second crystalline form, Form B, wherein said salt has an X-ray powder diffraction pattern substantially the same as the X-ray powder diffraction pattern shown in FIG. 8.

According to the present invention there is provided a maleate salt of AZD2171 in a second crystalline form, Form B, wherein said salt has an X-ray powder diffraction pattern with at least one specific peak at 2-theta=24.2° plus or minus 0.5° 2-theta.

According to the present invention there is provided a maleate salt of AZD2171 in a second crystalline form, Form B, wherein said salt has an X-ray powder diffraction pattern with at least one specific peak at 2-theta=22.7° plus or minus 0.5° 2-theta.

According to the present invention there is provided a maleate salt of AZD2171 in a second crystalline form, Form B, wherein said salt has an X-ray powder diffraction pattern with at least two specific peaks at 2-theta=24.2° and 22.7° wherein said values may be plus or minus 0.5° 2-theta.

According to the present invention there is provided a maleate salt of AZD2171 in a second crystalline form, Form B, wherein said salt has an X-ray powder diffraction pattern with specific peaks at 2-theta=24.2, 22.7, 15.7, 12.0, 27.1, 25.0, 17.7, 15.0, 23.1 and 12.6° wherein said values may be plus or minus 0.5° 2-theta.

According to the present invention there is provided a maleate salt of AZD2171 in a second crystalline form, Form B, wherein said salt has an X-ray powder diffraction pattern with at least one specific peak at 2-theta=24.2°.

According to the present invention there is provided a maleate salt of AZD2171 in a second crystalline form, Form B, wherein said salt has an X-ray powder diffraction pattern with at least one specific peak at 2-theta=22.7°.

According to the present invention there is provided a maleate salt of AZD2171 in a 5 second crystalline form, Form B, wherein said salt has an X-ray powder diffraction pattern with at least two specific peaks at 2-theta=24.2° and 22.7°.

According to the present invention there is provided a maleate salt of AZD2171 in a second crystalline form, Form B, wherein said salt has an X-ray powder diffraction pattern with specific peaks at 2-theta=24.2, 22.7, 15.7, 12.0, 27.1, 25.0, 17.7, 15.0, 23.1 and 12.6°.

According to the present invention there is provided a maleate salt of AZD2171 in a second crystalline form, Form B, wherein said salt has an X-ray powder diffraction pattern as shown in FIG. 8.

DSC analysis shows AZD2171 maleate Form B is a high melting solid with an onset of melting at 194.43° C. and a peak at 195.97° C. (FIG. 9).

Thus DSC analysis shows AZD2171 maleate Form B is a high melting solid with an onset of melting at about 194.43° C. and a peak at about 195.97° C.

Form B is meta-stable with respect to Form A (the melting point and heat of fusion of Form B are lower than those for Form A). Form A is the more thermodynamically stable form. A mixture of Form A and B converts to Form A upon slurrying in methanol at 40° C. for 4 days (FIG. 10).

Form A is preferred over Form B.

AZD2171 maleate is non-hygroscopic, absorbing <1% moisture at 80% relative humidity (FIG. 7).

The NMR details are given after the maleate salt preparation in Example 1 and show for the stoichiometry data a ratio of 1:1.

According to another aspect of the present invention there is provided a dimaleate salt of AZD2171. A dimaleate salt my be formed through the addition of two moles of maleic acid to one mole of AZD2171 free base.

When it is stated that the present invention relates to a crystalline form of AZD2171 free base, or AZD2171 maleate Form A or AZD2171 maleate Form B, the degree of crystallinity is conveniently greater than about 60%, more conveniently greater than about 80%, preferably greater than about 90% and more preferably greater than about 95%. Most preferably the degree of crystallinity is greater than about 98%.

The AZD2171 maleate salt forms A and B provide X-ray powder diffraction patterns substantially the same as the X-ray powder diffraction patterns shown in FIGS. 5 and 8 respectively and have substantially the ten most prominent peaks (angle 2-theta values) shown in Tables 3 and 4 respectively. It will be understood that the 2-theta values of the X-ray powder diffraction pattern may vary slightly from one machine to another or from one sample to another, and so the values quoted are not to be construed as absolute.

It is known that an X-ray powder diffraction pattern may be obtained which has one or more measurement errors depending on measurement conditions (such as equipment or machine used). In particular, it is generally known that intensities in an X-ray powder diffraction pattern may fluctuate depending on measurement conditions. Therefore it should be understood that the AZD2171 maleate salt forms of the present invention are not limited to the crystals that provide X-ray powder diffraction patterns identical to the X-ray powder diffraction patterns shown in FIGS. 5 and 8, and any crystals providing X-ray powder diffraction patterns substantially the same as those shown in FIGS. 5 and 8 fall within the scope of the present invention. A person skilled in the art of X-ray powder diffraction is able to judge the substantial identity of X-ray powder diffraction patterns.

Persons skilled in the art of X-ray powder diffraction will realise that the relative intensity of peaks can be affected by, for example, grains above 30 microns in size and non-unitary aspect ratios, which may affect analysis of samples. The skilled person will also realise that the position of reflections can be affected by the precise height at which the sample sits in the diffractometer and the zero calibration of the diffractometer. The surface planarity of the sample may also have a small effect. Hence the diffraction pattern data presented are not to be taken as absolute values. (Jenkins, R & Snyder, R. L. 'Introduction to X-Ray Powder Diffractometry' John Wiley & Sons 1996; Bunn, C. W. (1948), Chemical Crystallography, Clarendon Press, London; Klug, H. P. & Alexander, L. E. (1974), X-Ray Diffraction Procedures).

Generally, a measurement error of a diffraction angle in an X-ray powder diffractogram is about 5% or less, in particular plus or minus 0.5° 2-theta, and such degree of a measurement error should be taken into account when considering the X-ray powder diffraction patterns in FIGS. 2, 3, 4, 5, 8 and 10 and when reading Tables 1, 3 and 4. Furthermore, it should be understood that intensities may fluctuate depending on experimental conditions and sample preparation (preferred orientation).

For the avoidance of doubt, terms such as 'AZD2171 maleate salt' and 'a maleate salt of AZD2171' refer to each and every form of AZD2171 maleate salt, whereas 'AZD2171 maleate Form A' refers to the particular crystalline form known as Form A and 'AZD2171 maleate Form B' refers to the particular crystalline form known as Form B.

According to a further aspect of the invention there is provided a pharmaceutical composition which comprises an AZD2171 maleate salt as defined hereinbefore in association with a pharmaceutically acceptable excipient or carrier.

The composition may be in a form suitable for oral administration, (for example as tablets, lozenges, hard or soft capsules, aqueous or oily suspensions, emulsions, dispersible powders or granules, syrups or elixirs), for administration by inhalation (for example as a finely divided powder or a liquid aerosol), for administration by insufflation (for example as a finely divided powder), for parenteral injection (for example as a sterile solution, suspension or emulsion for intravenous, subcutaneous, intramuscular, intravascular or infusion dosing), for topical administration (for example as creams, ointments, gels, or aqueous or oily solutions or suspensions), or for rectal administration (for example as a suppository). Preferably AZD2171 maleate salt is administered orally. In general the above compositions may be prepared in a conventional manner using conventional excipients.

The compositions of the present invention are advantageously presented in unit dosage form. AZD2171 maleate will normally be administered to a warm-blooded animal at a unit dose within the range 1-50 mg per square meter body area of the animal, for example approximately 0.03-1.5 mg/kg in a human. A unit dose in the range, for example, 0.01-1.5 mg/kg, for example 0.05-0.75 mg/kg, preferably 0.03-0.5 mg/kg is envisaged and this is normally a therapeutically-effective dose. A unit dosage form such as a tablet or capsule will usually contain, for example 1-50 mg of active ingredient. Preferably a daily dose in the range of 0.03-0.5 mg/kg is employed. The size of the dose required for the therapeutic or prophylactic treatment of a particular disease state will necessarily be varied depending on the host treated, the route of administration and the severity of the illness being treated. Accordingly the optimum dosage may be determined by the practitioner who is treating any particular patient.

According to a further aspect of the present invention there is provided an AZD2171 maleate salt as defined hereinbefore for use in a method of treatment of the human or animal body by therapy.

A further feature of the present invention is an AZD2171 maleate salt as defined hereinbefore for use as a medicament, conveniently an AZD2171 maleate salt as defined hereinbefore for use as a medicament for producing an antiangiogenic and/or vascular permeability reducing effect in a warm-blooded animal such as a human being.

Thus according to a further aspect of the invention there is provided the use of an AZD2171 maleate salt as defined hereinbefore in the manufacture of a medicament for use in the production of an antiangiogenic and/or vascular permeability reducing effect in a warm-blooded animal such as a human being.

According to a further feature of the invention there is provided a method for producing an antiangiogenic and/or vascular permeability reducing effect in a warm-blooded animal, such as a human being, in need of such treatment which comprises administering to said animal an effective amount of an AZD2171 maleate salt as defined hereinbefore.

AZD2171 maleate salt is an antiangiogenic and/or vascular permeability reducing agent and may be applied as a sole therapy or may involve, in addition to AZD2171 maleate, one or more other substances and/or treatments. Such conjoint treatment may be achieved by way of the simultaneous, sequential or separate administration of the individual components of the treatment. In the field of medical oncology it is normal practice to use a combination of different forms of treatment to treat each patient with cancer. In medical oncology the other component(s) of such conjoint treatment in addition to AZD2171 maleate salt may be: surgery, radiotherapy or chemotherapy. Such chemotherapy may cover three main categories of therapeutic agent:

(i) other antiangiogenic agents such as those which inhibit the effects of vascular endothelial growth factor, (for example the anti-vascular endothelial cell growth factor antibody bevacizumab [Avastin™], and those that work by different mechanisms from those defined hereinbefore (for example linomide, inhibitors of integrin αvβ3 function, angiostatin, razoxin, thalidomide), and including vascular targeting agents (for example combretastatin phosphate and compounds disclosed in International Patent Applications WO00/40529, WO 00/41669, WO01/92224, WO02/04434 and WO02/08213 and the vascular damaging agents described in International Patent Application Publication No. WO 99/02166 the entire disclosure of which document is incorporated herein by reference, (for example N-acetylcolchinol-O-phosphate));

(ii) cytostatic agents such as antioestrogens (for example tamoxifen, toremifene, raloxifene, droloxifene, iodoxyfene), oestrogen receptor down regulators (for example fulvestrant), progestogens (for example megestrol acetate), aromatase inhibitors (for example anastrozole, letrazole, vorazole, exemestane), antiprogestogens, antiandrogens (for example flutamide, nilutamide, bicalutamide, cyproterone acetate), LHRH agonists and antagonists (for example goserelin acetate, luprolide, buserelin), inhibitors of 5α-reductase (for example finasteride), anti-invasion agents (for example metalloproteinase inhibitors like marimastat and inhibitors of urokinase plasminogen activator receptor function) and inhibitors of growth factor function, (such growth factors include for example platelet derived growth factor and hepatocyte growth factor), such inhibitors include growth factor antibodies, growth factor receptor antibodies, (for example the anti-erbb2 antibody trastuzumab [Herceptin™] and the anti-erbb1 antibody cetuximab [C225]), farnesyl transferase inhibitors, tyrosine kinase inhibitors for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, AZD1839), N-(3-ethynylphenyl)-6,7-bis (2-methoxyethoxy)quinazolin-4-amine (erlotinib, OSI-774) and 6-acrylamido-N-(3-chloro-4-fluorophenyl)-7-(3-morpholinopropoxy)quinazolin-4-amine (CI 1033)) and serine/threonine kinase inhibitors); and (iii) antiproliferative/antineoplastic drugs and combinations thereof, as used in medical oncology, such as antimetabolites (for example antifolates like methotrexate, fluoropyrimidines like 5-fluorouracil, tegafur, purine and adenosine analogues, cytosine arabinoside); antitumour antibiotics (for example anthracyclines like adriamycin, bleomycin, doxorubicin, daunomycin, epirubicin and idarubicin, mitomycin-C, dactinomycin, mithramycin); platinum derivatives (for example cisplatin, carboplatin); alkylating agents (for example nitrogen mustard, melphalan, chlorambucil, busulphan, cyclophosphamide, ifosfamide, nitrosoureas, thiotepa); antimitotic agents (for example vinca alkaloids like vincristine, vinblastine, vindesine, vinorelbine, and taxoids like taxol, taxotere); topoisomerase inhibitors (for example epipodophyllotoxins like etoposide and teniposide, amsacrine, topotecan, camptothecin and also irinotecan); also enzymes (for example asparaginase); and thymidylate synthase inhibitors (for example raltitrexed); and additional types of chemotherapeutic agent include:

(iv) biological response modifiers (for example interferon);
(v) antibodies (for example edrecolomab);
(vi) antisense therapies, for example those which are directed to the targets listed above, such as ISIS 2503, an anti-ras antisense;
(vii) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and
(viii) immunotherapy approaches, including for example ex-vivo and in vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

For example such conjoint treatment may be achieved by way of the simultaneous, sequential or separate administration of an AZD2171 maleate salt as defined hereinbefore and a vascular targeting agent described in WO 99/02166 such as N-acetylcolchinol-O-phosphate (Example 1 of WO 99/02166).

It is known from WO 01/74360 that antiangiogenics can be combined with antihypertensives. A salt of the present invention can also be administered in combination with an antihypertensive. An antihypertensive is an agent which lowers blood pressure, see WO 01/74360 which is incorporated herein by reference.

Thus according to the present invention there is provided a method of treatment of a disease state associated with angiogenesis which comprises the administration of an effective amount of a combination of an AZD2171 maleate salt as defined hereinbefore and an anti-hypertensive agent to a warm-blooded animal, such as a human being.

According to a further feature of the present invention there is provided the use of a combination of an AZD2171 maleate salt as defined hereinbefore and an anti-hypertensive agent for use in the manufacture of a medicament for the treatment of a disease state associated with angiogenesis in a warm-blooded mammal, such as a human being.

According to a further feature of the present invention there is provided a pharmaceutical composition comprising an AZD2171 maleate salt as defined hereinbefore and an anti-hypertensive agent for the treatment of a disease state associated with angiogenesis in a warm-blooded mammal, such as a human being.

According to a further aspect of the present invention there is provided a method for producing an anti-angiogenic and/or vascular permeability reducing effect in a warm-blooded animal, such as a human being, which comprises administering to said animal an effective amount of an AZD2171 maleate salt as defined hereinbefore and an anti-hypertensive agent.

According to a further aspect of the present invention there is provided the use of a combination of an AZD2171 maleate salt as defined hereinbefore and an anti-hypertensive agent for the manufacture of a medicament for producing an anti-angiogenic and/or vascular permeability reducing effect in a warm-blooded mammal, such as a human being.

Preferred antihypertensive agents are calcium channel blockers, angiotensin converting enzyme inhibitors (ACE inhibitors), angiotensin II receptor antagonists (A-II antagonists), diuretics, beta-adrenergic receptor blockers (β-blockers), vasodilators and alpha-adrenergic receptor blockers (α-blockers). Particular antihypertensive agents are calcium channel blockers, angiotensin converting enzyme inhibitors (ACE inhibitors), angiotensin II receptor antagonists (A-II antagonists) and beta-adrenergic receptor blockers (β-blockers), especially calcium channel blockers.

As stated above AZD2171 maleate salt is of interest for its antiangiogenic and/or vascular permeability reducing effects. AZD2171 maleate salt is expected to be useful in a wide range of disease states including cancer, diabetes, psoriasis, rheumatoid arthritis, Kaposi's sarcoma, haemangioma, lymphoedema, acute and chronic nephropathies, atheroma, arterial restenosis, autoimmune diseases, acute inflammation, excessive scar formation and adhesions, endometriosis, dysfunctional uterine bleeding and ocular diseases with retinal vessel proliferation including age-related macular degeneration. Cancer may affect any tissue and includes leukaemia, multiple myeloma and lymphoma. In particular such compounds of the invention are expected to slow advantageously the growth of primary and recurrent solid tumours of, for example, the colon, breast, prostate, lungs and skin. More particularly such compounds of the invention are expected to inhibit any form of cancer associated with VEGF including leukaemia, multiple myeloma and lymphoma and also, for example, the growth of those primary and recurrent solid tumours which are associated with VEGF, especially those tumours which are significantly dependent on VEGF for their growth and spread, including for example, certain tumours of the colon, breast, prostate, lung, brain vulva and skin.

In addition to their use in therapeutic medicine, the AZD2171 maleate salts defined hereinbefore are also useful as pharmacological tools in the development and standardisation of in vitro and in vivo test systems for the evaluation of the effects of inhibitors of VEGF receptor tyrosine kinase activity in laboratory animals such as cats, dogs, rabbits, monkeys, rats and mice, as part of the search for new therapeutic agents.

The assays written up in WO 00/47212 and used to test AZD2171 are as follows:

(a) In Vitro Receptor Tyrosine Kinase Inhibition Test

This assay determines the ability of a test compound to inhibit tyrosine kinase activity. DNA encoding VEGF, FGF or EGF receptor cytoplasmic domains may be obtained by total gene synthesis (Edwards M, International Biotechnology Lab 5(3), 19-25, 1987) or by cloning. These may then be expressed in a suitable expression system to obtain polypeptide with tyrosine kinase activity. For example VEGF, FGF and EGF receptor cytoplasmic domains, which were obtained by expression of recombinant protein in insect cells, were found to display intrinsic tyrosine kinase activity. In the case of the VEGF receptor Flt-1 (Genbank accession number X51602), a 1.7 kb DNA fragment encoding most of the cytoplasmic domain, commencing with methionine 783 and including the termination codon, described by Shibuya et al (Oncogene, 1990, 5: 519-524), was isolated from cDNA and cloned into a baculovirus transplacement vector (for example pAcYM1 (see The Baculovirus Expression System: A Laboratory Guide, L. A. King and R. D. Possee, Chapman and Hall, 1992) or pAc360 or pBlueBacHis (available from Invitrogen Corporation)). This recombinant construct was co-transfected into insect cells (for example *Spodoptera frugiperda* 21(Sf21)) with viral DNA (eg Pharmingen BaculoGold) to prepare recombinant baculovirus. (Details of the methods for the assembly of recombinant DNA molecules and the preparation and use of recombinant baculovirus can be found in standard texts for example Sambrook et al, 1989, Molecular cloning—A Laboratory Manual, 2nd edition, Cold Spring Harbour Laboratory Press and O'Reilly et al, 1992, Baculovirus Expression Vectors—A Laboratory Manual, W. H. Freeman and Co, New York). For KDR (Genbank accession number L04947), a cytoplasmic fragment starting from methionine 806 was cloned and expressed in a similar manner.

For expression of cFlt-1 tyrosine kinase activity, Sf21 cells were infected with plaque-pure cFlt-1 recombinant virus at a multiplicity of infection of 3 and harvested 48 hours later. Harvested cells were washed with ice cold phosphate buffered saline solution (PBS) (10 mM sodium phosphate pH7.4, 138 mM sodium chloride, 2.7 mM potassium chloride) then resuspended in ice cold HNTG/PMSF (20 mM Hepes pH7.5, 150 mM sodium chloride, 10% v/v glycerol, 1% v/v Triton X100, 1.5 mM magnesium chloride, 1 mM ethylene glycolbis((3-aminoethyl ether) N,N,N',N'-tetraacetic acid (EGTA), 1 mM PMSF (phenylmethylsulphonyl fluoride); the PMSF is added just before use from a freshly-prepared 100 mM solution in methanol) using 1 ml HNTG/PMSF per 10 million cells. The suspension was centrifuged for 10 minutes at 13,000 rpm at 4° C., the supernatant (enzyme stock) was removed and stored in aliquots at −70° C. Each new batch of stock enzyme was titrated in the assay by dilution with enzyme diluent (100 mM Hepes pH 7.4, 0.2 mM sodium orthovanadate, 0.1% v/v Triton X100, 0.2 mM dithiothreitol). For a typical batch, stock enzyme is diluted 1 in 2000 with enzyme diluent and 50 µl of dilute enzyme is used for each assay well.

A stock of substrate solution was prepared from a random copolymer containing tyrosine, for example Poly (Glu, Ala, Tyr) 6:3:1 (Sigma P3899), stored as 1 mg/ml stock in PBS at −20° C. and diluted 1 in 500 with PBS for plate coating.

On the day before the assay 100 µl of diluted substrate solution was dispensed into all wells of assay plates (Nunc maxisorp 96-well immunoplates) which were sealed and left overnight at 4° C.

On the day of the assay the substrate solution was discarded and the assay plate wells were washed once with PBST (PBS containing 0.05% v/v Tween 20) and once with 50 mM Hepes pH7.4.

Test compounds were diluted with 10% dimethylsulphoxide (DMSO) and 25 µl of diluted compound was transferred to wells in the washed assay plates. "Total" control wells contained 10% DMSO instead of compound. Twenty five microliters of 40 mM manganese(II)chloride containing 8 µM adenosine-5'-triphosphate (ATP) was added to all test wells except "blank" control wells which contained manganese(II) chloride without ATP. To start the reactions 50 µl of freshly diluted enzyme was added to each well and the plates were incubated at room temperature for 20 minutes. The liquid was then discarded and the wells were washed twice with PBST. One hundred microliters of mouse IgG anti-phosphotyrosine antibody (Upstate Biotechnology Inc. product 05-321), diluted 1 in 6000 with PBST containing 0.5% w/v bovine serum albumin (BSA), was added to each well and the plates were incubated for 1 hour at room temperature before discarding the liquid and washing the wells twice with PBST. One hundred microliters of horse radish peroxidase (HRP)-linked sheep anti-mouse Ig antibody (Amersham product NXA 931), diluted 1 in 500 with PBST containing 0.5% w/v BSA, was added and the plates were incubated for 1 hour at room temperature before discarding the liquid and washing the wells twice with PBST. One hundred microliters of 2,2'-azino-bis(3-ethylbenzthiazoline-6-sulphonic acid) (ABTS) solution, freshly prepared using one 50 mg ABTS tablet (Boehringer 1204 521) in 50 ml freshly prepared 50 mM phosphate-citrate buffer pH5.0+0.03% sodium perborate (made with 1 phosphate citrate buffer with sodium perborate (PCSB) capsule (Sigma P4922) per 100 ml distilled water), was added to each well. Plates were then incubated for 20-60 minutes at room temperature until the optical density value of the "total" control wells, measured at 405 nm using a plate reading spectrophotometer, was approximately 1.0. "Blank" (no ATP) and "total" (no compound) control values were used to determine the dilution range of test compound which gave 50% inhibtion of enzyme activity.

(b) In Vitro HUVEC Proliferation Assay

This assay determines the ability of a test compound to inhibit the growth factor-stimulated proliferation of human umbilical vein endothelial cells (HUVEC).

HUVEC cells were isolated in MCDB 131 (Gibco BRL)+ 7.5% v/v foetal calf serum (FCS) and were plated out (at passage 2 to 8), in MCDB 131+2% v/v FCS+3 µg/ml heparin+1 µg/ml hydrocortisone, at a concentration of 1000 cells/ well in 96 well plates. After a minimum of 4 hours they were dosed with VEGF (3 ng/ml) and compound. The cultures were then incubated for 4 days at 37° C. with 7.5% $CO_2$. On day 4 the cultures were pulsed with 1 µCi/well of tritiated-thymidine (Amersham product TRA 61) and incubated for 4 hours. The cells were harvested using a 96-well plate harvester (Tomtek) and then assayed for incorporation of tritium with a Beta plate counter. Incorporation of radioactivity into cells, expressed as cpm, was used to measure inhibition of growth factor-stimulated cell proliferation by compounds. This methodology was also used to assess compound effects versus basal HUVEC growth (i.e. endothelial cell proliferation in MCDB 131+2% v/v FCS+3 µg/ml heparin+1 µg/ml hydrocortisone without the addition of exogenous VEGF).

(c) In Vivo Solid Tumour Disease Model

This test measures the capacity of compounds to inhibit solid tumour growth.

CaLu-6 tumour xenografts were established in the flank of female athymic Swiss nu/nu mice, by subcutaneous injection of $1 \times 10^6$ Calu-6 cells/mouse in 100 µl of a 50% (v/v) solution of Matrigel in serum free culture medium. Ten days after cellular implant, mice were allocated to groups of 8-10, so as to achieve comparable group mean volumes. Tumours were measured using vernier calipers and volumes were calculated as: $(l \times w) \times \sqrt{(l \times w)} \times (\pi/6)$, where $l$ is the longest diameter and $w$ the diameter perpendicular to the longest. Test compounds were administered orally once daily for a minimum of 21 days, and control animals received compound diluent. Tumours were measured twice weekly. The level of growth inhibition was calculated by comparison of the mean tumour volume of the control group versus the treatment group using a Student T test and/or a Mann-Whitney Rank Sum Test. The inhibitory effect of compound treatment was considered significant when $p<0.05$.

An AZD2171 maleate salt as defined hereinbefore may be prepared by any process known to be applicable to the preparation of chemically-related compounds. Such processes include, for example, those illustrated in International Patent Application No. WO 00/47212 all of which are incorporated herein by reference. Such processes also include, for example, solid phase synthesis. Such processes, are provided as a further feature of the invention and are as described hereinafter. Necessary starting materials may be obtained by standard procedures of organic chemistry. AZD2171 free base may be prepared according to any of the processes described in WO 00/47212, see in particular Example 240 of WO 00/47212. Alternatively necessary starting materials are obtainable by analogous procedures to those illustrated which are within the ordinary skill of an organic chemist.

The following processes (a) (b) and (c) constitute further features of the present invention.

Synthesis of AZD2171 Maleate Salt Form A (a) Such a process provides a further aspect of the present invention and comprises, for example, the steps of:
  (i) dissolving AZD2171 free base in an organic solvent to form a solution;
  (ii) adding an aqueous solution of maleic acid or adding a solution of maleic acid in an organic solvent;
  (iii) allowing spontaneous nucleation to occur;
  (iv) optionally isolating the crystalline mixture of AZD2171 Forms A and B so formed;
  (v) slurrying the mixture in a solvent, for example methanol, until all the AZD2171 maleate is Form A, (as may be determined by X-Ray Powder Diffraction), for example this may take 4 days; and
  (vi) isolating the crystalline solid so formed.

(b) Another such process provides a further aspect of the present invention and comprises, for example, the steps of:
  (i) dissolving AZD2171 free base in an organic solvent to form a solution;
  (ii) adding an aqueous solution of maleic acid or adding a solution of maleic acid in an organic solvent;
  (iii) obtaining a solution, for example by heating or adding more solvent, and adding a seed of AZD2171 maleate Form A to initiate crystallisation of AZD2171 maleate Form A; and
  (iv) isolating the crystalline solid so formed.

For part (i) of (a) and (b) the mixture may, if required, be heated to reflux until dissolution has occurred. Alternatively, the mixture may, for example, be heated to a temperature less than the reflux temperature of the solvent provided that dissolution of more or less all of the solid material has occurred. It will be appreciated that small quantities of insoluble material may be removed by filtration of the warmed mixture.

For part (i) of (a) and (b) the organic solvent is preferably an alcohol, for example methanol or isopropanol.

For part (ii) of (a) and (b) the organic solvent is preferably an alcohol, for example methanol.

(c) Synthesis of AZD2171 Maleate Salt Form B

Such a process provides a further aspect of the present invention and comprises, for example, the steps of:
  (i) dissolving AZD2171 maleate in an organic solvent to form a solution;
  (ii) adding the solution to a solvent in which AZD2171 maleate has a lower solubility than it does in NMP, for example toluene or ethyl acetate;
  (iii) crystallisation of AZD2171 maleate Form B then occurs; and
  (iv) isolating the crystalline solid so formed.

In (c) a preferred organic solvent is a highly solubilising solvent such as 1-methyl-2-pyrrolidinone.

For part (i) of (c) the mixture may, if required, be heated to reflux until dissolution has occurred. Alternatively, the mixture may, for example, be heated to a temperature less than the reflux temperature of the solvent provided that dissolution of more or less all of the solid material has occurred. It will be appreciated that small quantities of insoluble material may be removed by filtration of the warmed mixture.

In (a), (b) and (c) above the crystalline solid so formed may be isolated by any conventional method, for example by filtration.

The invention is illustrated hereinafter by means of the following non-limiting Examples, data and Figures in which, unless otherwise stated: —

(i) evaporations were carried out by rotary evaporation in vacuo and work-up procedures were carried out after removal of residual solids such as drying agents by filtration;

(ii) yields are given for illustration only and are not necessarily the maximum attainable;

(iii) melting points are uncorrected and were determined using a Mettler DSC820e;

(iv) the structures of the end-products of the formula I were confirmed by nuclear (generally proton) magnetic resonance (NMR) and mass spectral techniques; proton magnetic resonance chemical shift values were measured on the delta scale and peak multiplicities are shown as follows: s, singlet; d, doublet; t, triplet; m, multiplet; br, broad; q, quartet; quin, quintet; all samples run on a Bruker DPX 400 MHz at 300K in $d_6$-DMSO, 16 scans, pulse repetition time 10 seconds;

(v) intermediates were not generally fully characterised and purity was assessed by NMR analysis; and (vi) the following abbreviations have been used: —
DMSO dimethylsulphoxide
NMP 1-methyl-2-pyrrolidinone Example 1

AZD2171 Maleate Form A

Under an inert atmosphere of nitrogen AZD2171 crude free base (4.52 g), (prepared for example as described in Example 240 of WO 00/47212) was slurried with isopropanol (58.8 mL). The mixture was heated at reflux for 15 minutes to give a clear, dark solution. The mixture was cooled to 75° C.

and charcoal (0.226 g) added. The mixture was reheated to reflux and held at reflux for an hour. The mixture was then filtered hot. The charcoal filter cake was washed with hot isopropanol (9 mL). The temperature of the combined filtrate and wash was adjusted to 55° C. and a prefiltered solution of maleic acid (1.173 g) in water (2.71 mL) was added dropwise over 5 minutes. The crude free base which previously crystallised dissolved during the addition. A line wash of water (0.9 mL) was added. The mixture was maintained at 55° C. for 15 minutes and a seed of AZD2171 maleate Form A (0.023 g) added. The mixture was held at 55° C. for 4 hours. During the 4 hour hold crystallisation became established. The mixture was cooled to 0° C. over 8 hours. The mixture was held at 0° C. for a minimum of 8 hours. The mixture was filtered. The cake was washed with isopropanol (9 mL). The solid was dried in a vacuum oven at 50° C. to give 4-([4-fluoro-2-methyl-1H-indol-5-yl]oxy)-6-methoxy-7-(3-(pyrrolidin-1-yl)propoxy)quinazoline maleate Form A. $^1$H NMR Spectrum: (400 MHz, DMSO): 11.36 (s, 1H), 8.53 (s, 1H), 7.65 (s, 1H), 7.43 (s, 1H), 7.18 (d, 1H), 7.01 (d, 1H), 6.25 (s, 1H), 6.04 (s, 2H), 4.33 (t, 2H), 4.02 (s, 3H), 3.26-3.3.70 (b, 4H), 2.44, (s, 3H), 2.24 (m, 2H), 2.02 (m, 4H).

m.p.: DSC analysis: onset of melting at 198.3° C. and a peak at 200.08° C.

Example 2

AZD2171 Maleate Form A

Under an inert atmosphere of nitrogen AZD2171 crude free base (23.0 g) (prepared for example as described in Example 240 of WO 00/47212) was slurried in methanol (223 mL) in vessel 1. The mixture was degassed by holding under vacuum and then releasing the vacuum with nitrogen. This was repeated five times. The slurry was then heated to reflux and held there for 15 minutes to give a clear, dark brown solution. The solution was cooled to 60° C. and then filtered through a Celite® pad (4.00 g) into vessel 2. The Celite® pad was washed with hot (60° C.) methanol (78 mL), the filtrate again going to vessel 2.

To vessel 1 was then charged methanol (111 mL), which was cooled to 0° C. To vessel 1 was then charged maleic acid (5.50 g) and the mixture stirred at 0° C. for 15 minutes until all the maleic acid had dissolved.

The contents of vessel 1 were then charged to vessel 2 through an in-line filter whilst maintaining the temperature above 52° C. A seed of AZD2171 maleate Form A (0.0454 g) was added to vessel 2 at 55° C. and the mixture held at 55° C. for 3 hours. The mixture was then cooled to 40° C. over 7 hours, then cooled further to −5° C. over 6 hours. The solid was filtered and washed with methanol (100 mL) at −5° C. The product was dried in a vacuum oven for 24 hours to give 4-([4-fluoro-2-methyl-1H-indol-5-yl]oxy)-6-methoxy-7-(3-(pyrrolidin-1-yl)propoxy)quinazoline maleate Form A.

Example 3

AZD2171 Maleate Form B

AZD2171 maleate Form A (2.31 g) was dissolved in warm (~50° C.) NMP. This solution was added dropwise to toluene (23 mL) over 2 minutes at ambient temperature. Material originally precipitated as a solid then became an oil, then a solid again. After stirring for 10 minutes at ambient temperature the solid was filtered and washed with toluene (10 mL). The solid was dried in a vacuum oven at ambient temperature overnight to give 4-((4-fluoro-2-methyl-1H-indol-5-yl)oxy)-6-methoxy-7-(3-(pyrrolidin-1-yl)propoxy)quinazoline maleate Form B.

m.p.: DSC analysis: onset of melting at 194.43° C. and a peak at 195.97° C.

BRIEF DESCRIPTION OF THE DRAWINGS

FIG. 1: DSC and TGA Thermograms for AZD2171 Free base Monohydrate—with temperature in ° C. plotted on the horizontal axis and heat flow/% weight loss on the vertical axis FIG. 2: X-Ray Powder Diffraction Pattern for AZD2171 free base—with the 2θ values plotted on the horizontal axis and the relative line intensity (count) plotted on the vertical axis.

FIG. 3: X-Ray Powder Diffraction Pattern for AZD2171 Free base Monohydrate Heated to 100° C.—with the 2θ values plotted on the horizontal axis and the relative line intensity (count) plotted on the vertical axis.

FIG. 4: X-Ray Powder Diffraction Pattern for AZD2171 Free base Micronised—with the 2θ values plotted on the horizontal axis and the relative line intensity (count) plotted on the vertical axis.

FIG. 5: X-Ray Powder Diffraction Pattern for AZD2171 Maleate Salt Form A—with the 2θ values plotted on the horizontal axis and the relative line intensity (count) plotted on the vertical axis.

FIG. 6: DSC Thermogram for AZD2171 Maleate Form A—with temperature in ° C. plotted on the horizontal axis and endothermic heat flow (milliWatts (mW)) plotted on the vertical axis.

FIG. 7: AZD2171 Maleate Form A Vapour Sorption Isotherm at 25° C.—with target relative humidity (RH) (%) plotted on the horizontal axis and change in dry mass (%) plotted on the vertical axis.

FIG. 8: X-Ray Powder Diffraction Pattern AZD2171 Maleate Salt Form B—with the 2θ values plotted on the horizontal axis and the relative line intensity (count) plotted on the vertical axis.

FIG. 9: DSC Thermogram for AZD2171 Maleate Form B—with temperature in ° C. plotted on the horizontal axis and endothermic heat flow (milliWatts (mW)) plotted on the vertical axis.

FIG. 10: X-Ray Powder Diffraction Patterns for AZD2171 Maleate Slurry Experiment with the 2θ values plotted on the horizontal axis and the relative line intensity (count) plotted on the vertical axis.

DETAILS OF TECHNIQUES USED

X-Ray Powder Diffraction

TABLE 5

| % Relative Intensity* | Definition |
|---|---|
| 25-100 | vs (very strong) |
| 10-25 | s (strong) |
| 3-10 | m (medium) |
| 1-3 | w (weak) |

*The relative intensities are derived from diffractograms measured with fixed slits
Analytical Instrument: Siemens D5000

The X-ray powder diffraction spectra were determined by mounting a sample of the crystalline salt on Siemens single silicon crystal (SSC) wafer mounts and spreading out the sample into a thin layer with the aid of a microscope slide. The sample was spun at 30 revolutions per minute (to improve counting statistics) and irradiated with X-rays generated by a copper long-fine focus tube operated at 40 kV and 40 mA with a wavelength of 1.5406 angstroms. The collimated X-ray source was passed through an automatic variable divergence slit set at V20 and the reflected radiation directed through a 2 mm antiscatter slit and a 0.2 mm detector slit. The sample was exposed for 1 second per 0.02 degree 2-theta increment (continuous scan mode) over the range 2 degrees to 40 degrees 2-theta in theta-theta mode. The running time was 31 minutes and 41 seconds. The instrument was equipped with a scintillation counter as detector. Control and data capture was by means of a Dell Optiplex 686 NT 4.0 Workstation operating with Diffract+ software. Persons skilled in the art of X-ray powder diffraction will realise that the relative intensity of peaks can be affected by, for example, grains above 30 microns in size and non-unitary aspect ratios which may affect analysis of samples. The skilled person will also realise that the position of reflections can be affected by the precise height at which the sample sits in the diffractometer and the zero calibration of the diffractometer. The surface planarity of the sample may also have a small effect. Hence the diffraction pattern data presented are not to be taken as absolute values.

Sieving/Micronisation

AZD2171 free base was sieved prior to Micronising using a 1 mm stainless steel sieve, the base being used for product collection and for manual feeding directly into the microniser. Approximately 7.5 g of AZD2171 free base was sieved.
A clean S/S lined 2" Microniser was used.
Manual feed rate: approximately 2/3 g per minute.
Grind air pressure range 10/20 psi (0.67/1.33 atmospheres).
Venturi air pressure range 20/25 psi (1.33/1.67 atmospheres).

Dynamic Vapour Sorption

Analytical Instrument: Surface Measurements Systems Dynamic Vapour Sorption Analyser.
About 5 mg of material contained in a quartz holder at 25° C. was subjected to humidified nitrogen at the following relative humidities (RH): 0, 20, 40, 60, 80, 95, 80, 60, 40, 20, 0% RH in duplicate.

Differential Scanning Calorimetry

Analytical Instrument: Mettler DSC820e.
Typically less than 5 mg of material contained in a 40 μl aluminium pan fitted with a pierced lid was heated over the temperature range 25° C. to 325° C. at a constant heating rate of 10° C. per minute. A purge gas using nitrogen was used—flow rate 100 ml per minute.

Thermogravimetric Analysis

Analytical Instrument: Mettler TG851.
Typically between 3 and 12 mg of material contained in a 70 μl alox (aluminium oxide) crucible was heated over the temperature range 25° C. to 325° C. at a constant heating rate of 10° C. per minute. A purge gas using helium was used—flow rate 50 ml per minute.

Karl Fischer Water Content

Analytical Instrument: Mitsubishi Moisture Meter CA-05.
Typically approximately 50 mg of material was used.

The invention claimed is:

1. A maleate salt of 4-((-fluoro-2-methyl-1H-indol-5-yl)oxy)-6-methoxy-7-(3-(pyrrolidin-1-yl)propoxy)quinazoline in a Form A crystalline form, wherein the salt has at least three XRPD peaks selected from 21.5, 16.4 and 24.4 degrees theta.

2. A maleate salt of b 4-((-fluoro-2-methyl-1H-indol-5-yl)oxy)-6-methoxy-7-(3-(pyrrolidin-1-yl)propoxy)quinazoline in a Form B crystalline form, wherein the salt has at least three XRPD peaks selected from 24.2, 22.7 and 15.7 degrees theta.

3. The maleate salt according to claim 1, wherein the salt has XRPD peaks selected from 21.5, 16.4, 24.4, 20.7, 25.0, 16.9, 12.1, 22.2, 17.4 and 17.6 degrees theta.

4. The maleate salt according to claim 1, wherein the salt has an XRPD pattern substantially the same as the XRPD pattern shown in FIG. 5.

5. The maleate salt according to claim 2, wherein the salt has XRPD peaks selected from 24.2, 22.7, 15.7, 12.0, 27.1, 25.0, 17.7, 15.0, 23.1 and 12.6 degrees theta.

6. The maleate salt according to claim 2, wherein the salt has an XRPD pattern substantially the same as the XRPD pattern shown in FIG. 8.

7. A pharmaceutical composition comprising the maleate salt according to claim 1 in association with a pharmaceutically acceptable excipient or carrier.

8. A pharmaceutical composition comprising the maleate salt according to claim 2 in association with a pharmaceutically acceptable excipient or carrier.

9. A process for the preparation of the maleate salt according to claim 1, which comprises:
 (i) dissolving 4-((-fluoro-2-methyl-1H-indol-5-yl)oxy)-6-methoxy-7-(3-(pyrrolidin-1-yl)propoxy)quinazoline free base in an organic solvent to form a solution;
 (ii) adding an aqueous solution of maleic acid or adding a solution of maleic acid in an organic solvent;
 (iii) allowing spontaneous nucleation to occur;
 (iv) slurrying the resulting maleate salt of 4-((-fluoro-2-methyl-1H-indol-5-yl)oxy)-6-methoxy-7-(3-(pyrrolidin-1-yl)propoxy)quinazoline in a solvent until all the maleate salt is of Form A; and
 (v) isolating the Form A maleate salt.

10. A process for the preparation of the maleate salt according to claim 1, which comprises:
 (i) dissolving 4-((-fluoro-2-methyl-1H-indol-5-yl)oxy)-6-methoxy-7-(3-(pyrrolidin-1-yl)propoxy)quinazoline free base in an organic solvent to form a solution;
 (ii) adding an aqueous solution of maleic acid or adding a solution of maleic acid in an organic solvent;
 (iii) obtaining a solution and adding a seed of the Form A maleate salt to initiate crystallisation; and
 (iv) isolating the Form A maleate salt so formed as a crystalline solid.

11. A process for the preparation of the maleate salt according to claim 2, which comprises:
 (i) dissolving 4-((-fluoro-2-methyl-1H-indol-5-yl)oxy)-6-methoxy-7-(3-(pyrrolidin-1-yl)propoxy)quinazoline maleate salt in an organic solvent to form a solution;
 (ii) adding the solution to a solvent in which the 4-((-fluoro-2-methyl-1H-indol-5-yl)oxy)-6-methoxy-7-(3-(pyrrolidin-1-yl)propoxy)quinazoline maleate salt has a lower solubility than it does in NMP, which results in crystallization of the Form B maleate salt; and
 (iii) isolating the Form B maleate salt as a crystalline solid.

* * * * *

UNITED STATES PATENT AND TRADEMARK OFFICE
CERTIFICATE OF CORRECTION

PATENT NO. : 8,859,570 B2
APPLICATION NO. : 12/646153
DATED : October 14, 2014
INVENTOR(S) : James McCabe Page 1 of 2

It is certified that error appears in the above-identified patent and that said Letters Patent is hereby corrected as shown below:

In the Claims

Claim 1, col. 19, line 59, "4-((-fluoro-2-methyl-1H-indol-5-yl)" should read -- 4-((4-fluoro-2-methyl-1H-indol-5-yl) --.

Claim 1, col. 19, line 60, "oxy)-6 -methoxy-7-(3-(pyrrolidin-1-yl)propoxy)quinazoline" should read -- oxy)-6-methoxy-7-(3-(pyrrolidin-1-yl)propoxy)quinazoline --.

Claim 1, col. 20, line 2, "theta" should read -- 2-theta --.

Claim 2, col. 20, line 3, "b 4-((-fluoro-2-methyl-1H-indol-5-yl)" should read -- 4-((4-fluoro-2-methyl-1H-indol-5-yl) --.

Claim 2, col. 20, line 4, "oxy)-6 -methoxy-7-(3-(pyrrolidin-1-yl)propoxy)quinazoline" should read -- oxy)-6-methoxy-7-(3-(pyrrolidin-1-yl)propoxy)quinazoline --.

Claim 2, col. 20, line 6, "theta" should read -- 2-theta --.

Claim 3, col. 20, line 9, "theta" should read -- 2-theta --.

Claim 5, col. 20, line 14, "theta" should read -- 2-theta --.

Claim 9, col. 20, line 26, "4-((-fluoro-2-methyl-1H-indol-5-yl)oxy)-" should read -- 4-((4-fluoro-2-methyl-1H-indol-5-yl)oxy)- --.

Claim 9, col. 20, line 27, "6 -methoxy-7-(3-(pyrrolidin-1-yl)propoxy)quinazoline" should read -- 6-methoxy-7-(3-(pyrrolidin-1-yl)propoxy)quinazoline --.

Claim 9, col. 20, line 32, "4-((-fluoro-2-" should read -- 4-((4-fluoro-2- --.

Signed and Sealed this
Fifth Day of May, 2015

Michelle K. Lee
*Director of the United States Patent and Trademark Office*

CERTIFICATE OF CORRECTION (continued)
U.S. Pat. No. 8,859,570 B2

Claim 9, col. 20, line 33, "methyl-1H-indol-5-yl-oxy)-6 -methoxy-7-(3-(pyrroli-" should read -- methyl-1H-indol-5-yl-oxy)-6-methoxy-7-(3-(pyrroli- --.

Claim 10, col. 20, line 39, "4-((-fluoro-2-methyl-1H-indol-5-yl)oxy)-" should read -- 4-((4-fluoro-2-methyl-1H-indol-5-yl)oxy)- --.

Claim 10, col. 20, line 40, "6 -methoxy-7-(3-(pyrrolidin-1-yl)propoxy)quinazoline" should read -- 6-methoxy-7-(3-(pyrrolidin-1-yl)propoxy)quinazoline --.

Claim 11, col. 20, line 50, "4-((-fluoro-2-methyl-1H-indol-5-yl)oxy)-" should read -- 4-((4-fluoro-2-methyl-1H-indol-5-yl)oxy)- --.

Claim 11, col. 20, line 51, "6 -methoxy-7-(3-(pyrrolidin-1-yl)propoxy)quinazoline" should read -- 6-methoxy-7-(3-(pyrrolidin-1-yl)propoxy)quinazoline --.

Claim 11, col. 20, line 54, "4-((-fluoro-2-methyl-1H-indol-5-yl)oxy)-6 -methoxy-" should read -- 4-((4-fluoro-2-methyl-1H-indol-5-yl)oxy)- 6-methoxy- --.